United States Patent [19]

Brace

[11] Patent Number: 5,547,131
[45] Date of Patent: Aug. 20, 1996

[54] DISPENSING DEVICE WITH SPRAY NOZZLE AND DRIVEN PISTON

[75] Inventor: Geoffrey Brace, Norfolk, United Kingdom

[73] Assignee: Bespak plc, United Kingdom

[21] Appl. No.: 253,581

[22] Filed: Jun. 3, 1994

Related U.S. Application Data

[63] Continuation of Ser. No. 927,396, filed as PCT/GB91/00532 Apr. 5, 1991, abandoned.

[51] Int. Cl.⁶ ................................................. A61M 5/315
[52] U.S. Cl. ........................ 239/309; 239/329; 239/463; 239/570; 239/579; 239/324; 222/390; 128/200.23
[58] Field of Search .................................. 239/309, 314, 239/320, 324, 579, 530, 463, 570; 222/324, 385, 386, 390, 513, 514, 518, 525, 559, 563, 530, 3; 128/200.23, 200.21

[56] References Cited

U.S. PATENT DOCUMENTS

| | | | |
|---|---|---|---|
| 731,659 | 6/1903 | Bennett | 222/514 |
| 1,707,660 | 4/1929 | Hammerstein | 222/514 |
| 2,631,757 | 3/1953 | Alexander | 128/200.23 X |
| 2,677,373 | 5/1954 | Barradas | 239/309 X |
| 3,162,194 | 12/1964 | Indelicato | 239/309 X |
| 3,203,592 | 8/1965 | Farandatos | 222/518 X |
| 3,306,252 | 2/1967 | Knight et al. | 128/220.23 X |
| 3,367,330 | 2/1968 | Sierpen | 128/220.23 |
| 3,856,185 | 12/1974 | Riccio | 239/309 X |
| 4,165,739 | 8/1979 | Doherty et al. | |
| 4,393,884 | 7/1983 | Jacobs | 128/200.23 X |
| 4,883,204 | 11/1989 | Kay et al. | 222/385 X |
| 5,062,830 | 11/1991 | Dunlap | 604/72 X |

FOREIGN PATENT DOCUMENTS

| | | |
|---|---|---|
| 0028173 | 5/1981 | European Pat. Off. . |
| 0308100 | 3/1989 | European Pat. Off. . |
| 0338806 | 10/1989 | European Pat. Off. . |
| 2574318 | 6/1986 | France . |
| 2628011 | 9/1989 | France . |
| 184313 | 3/1905 | Germany . |
| 624643 | 1/1936 | Germany ........................ 128/200.23 |
| 553149 | 5/1943 | United Kingdom . |
| 0728816 | 4/1955 | United Kingdom . |
| 1531760 | 11/1978 | United Kingdom . |
| 1587113 | 4/1981 | United Kingdom . |
| 2132896 | 7/1984 | United Kingdom . |
| 2209564 | 5/1989 | United Kingdom . |
| WO88/09189 | 12/1988 | WIPO . |

*Primary Examiner*—Kevin P. Weldon
*Attorney, Agent, or Firm*—Beveridge, DeGrandi, Weilacher & Young, L.L.P.

[57] ABSTRACT

A dispensing device which includes a container for liquid to be dispensed, an outlet nozzle including a device to break-up a flow of liquid under pressure into a spray, a piston for forcing liquid out of the container under pressure and through the nozzle, and a drive device for moving the piston a predetermined distance to dispense a predetermined quantity of liquid from the container. The drive device includes a dose selector for selecting the predetermined amount of liquid and a plunger for moving the piston, movement of the dose selector determining subsequent movement of the plunger. The device is particularly suited to nasal administration of liquid.

18 Claims, 7 Drawing Sheets

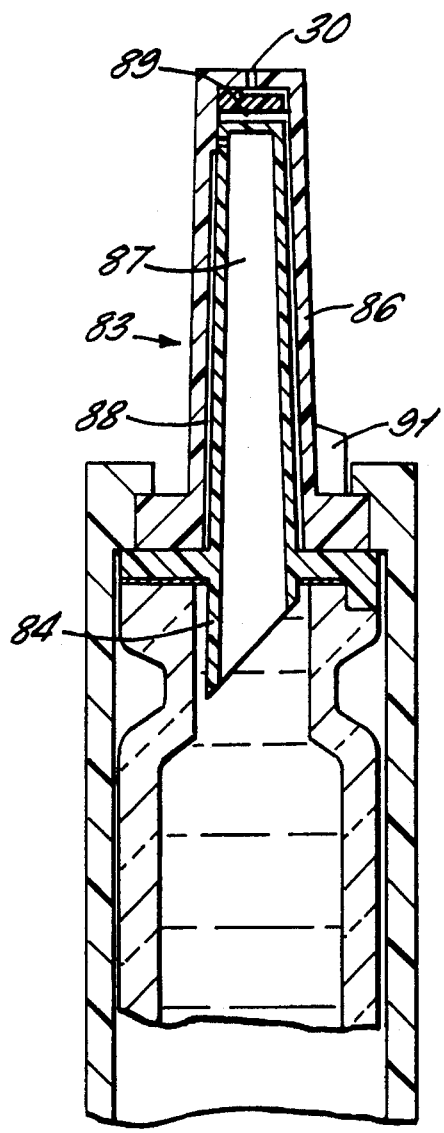
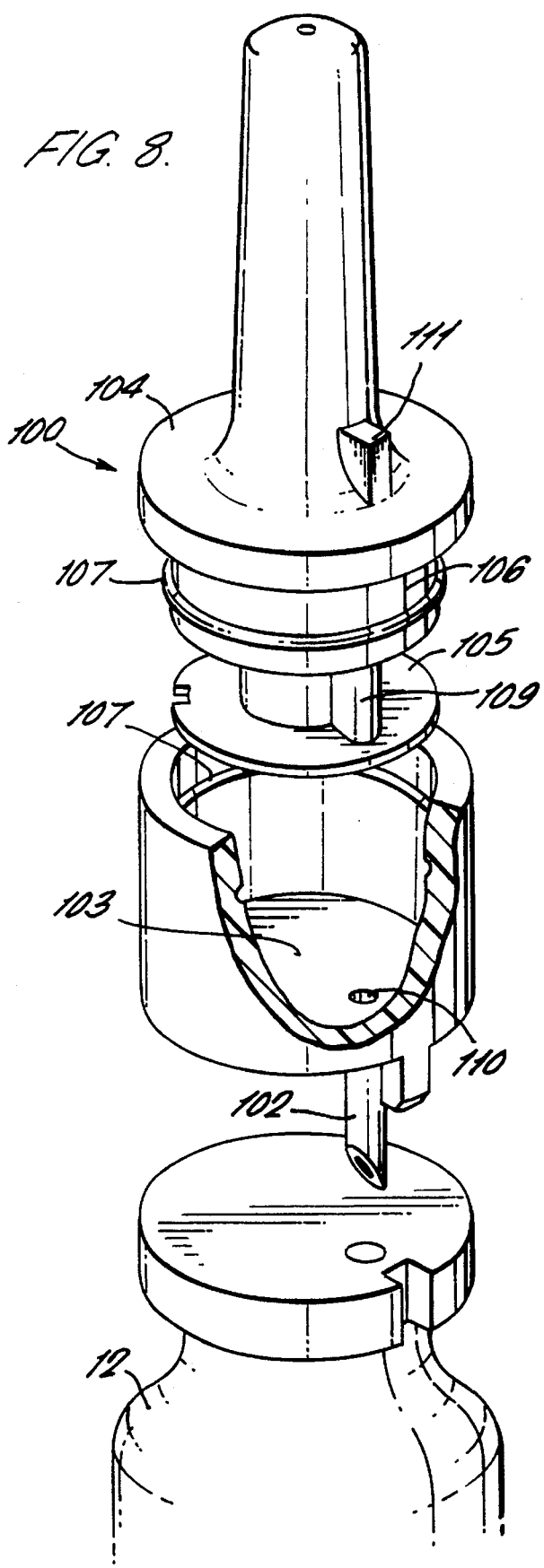

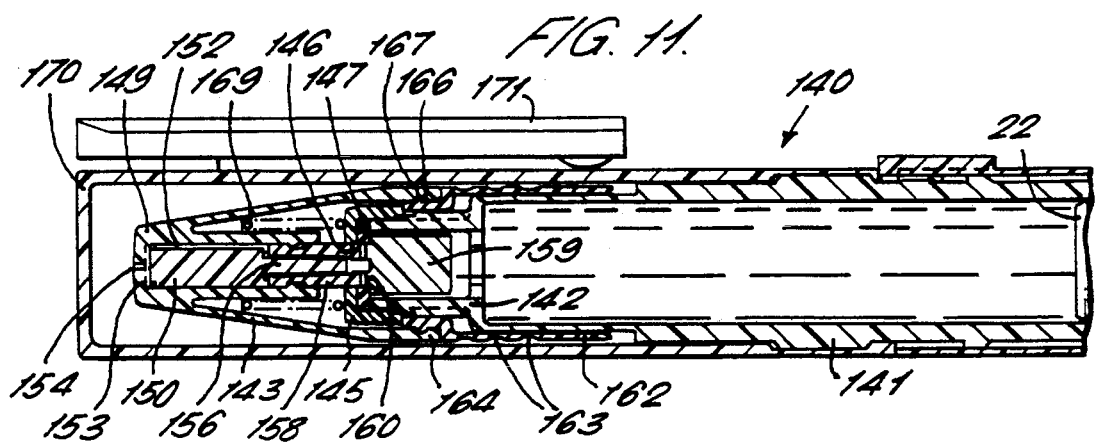
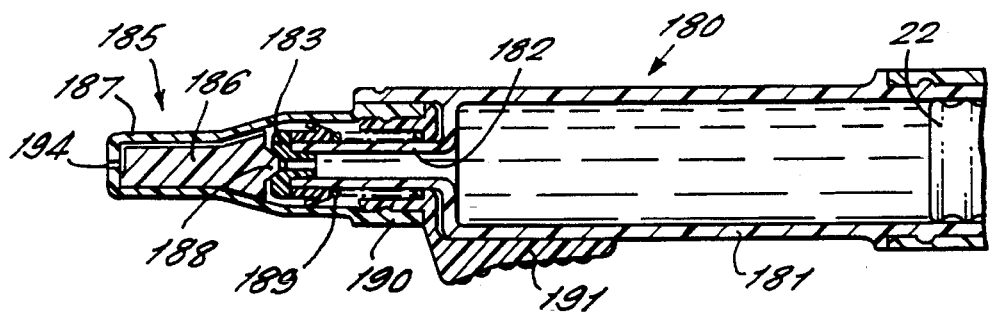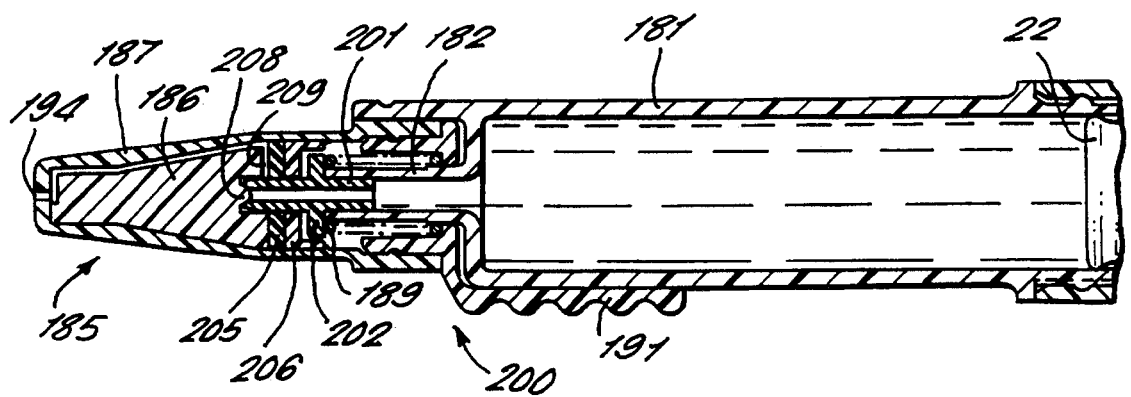

5,547,131

DISPENSING DEVICE WITH SPRAY NOZZLE AND DRIVEN PISTON

This application is a continuation of abandoned application Ser. No. 07/927,396, now abandoned, and originating from PCT/GB91/00532 filed on Apr. 5, 1991.

FIELD OF THE INVENTION

The invention relates to dispensing devices and particularly to dispensing devices for dispensing liquid medicaments such as insulin in a spray form.

SUMMARY OF THE INVENTION

The invention provides a dispensing device comprising a container for liquid to be dispensed, an outlet nozzle including means to break-up a flow of liquid under pressure into a spray, a piston for forcing liquid out of the container under pressure and through the nozzle, and drive means for moving the piston a predetermined distance to dispense a predetermined quantity of liquid from the container.

Preferably the drive means includes a dose selector for selecting the predetermined amount of liquid. The drive means may include a plunger for moving the piston, movement of the dose selector determining subsequent movement of the plunger. The movement of the dose selector may store energy in a spring, a trigger being provided for releasing the spring and thereby moving the plunger.

Sealing means may be provided for selectively closing the flow path from the container through the nozzle. The sealing means may comprise valve means in the nozzle, the valve means being resiliently urged into a closed position and opened by flow of liquid under pressure from the container.

Alternatively, the sealing means may comprise means for moving one component of the nozzle relative to another to open and close the flow path.

In a further embodiment, the sealing means may comprise a spike of the nozzle extending into the container through a seal of the container and means for moving a part of the nozzle and the spike axially relative to the container.

Preferably the sealing means comprise valve means normally urged into a closed position, the trigger means being arranged to open the valve means.

The valve means may be opened by relative movement between the nozzle and the container. The device may further comprise a manually operable sliding member fixed to the nozzle for moving the nozzle relative to the container and the valve means may be located between the container and the nozzle.

Preferably the valve means comprise a valve seat formed in a component fixed to the container and a valve member fixed to or integral with the nozzle and co-operable with the valve seat to close off the flow path from the container through the nozzle.

The valve means may be opened by relative axial movement of the nozzle towards, or away from, the container.

The container, piston and nozzle may form a disposable unit, the unit including means at an end remote from the nozzle for connecting said unit to the drive means.

BRIEF DESCRIPTION

Some preferred embodiments of the invention will now be described, by way of example, with reference to the accompanying drawings, in which:

FIG. 7 is a view similar to FIG. 6 showing a further alternative sealing arrangement:

FIG. 8 is an exploded view of a further embodiment of nozzle assembly for the dispensing device showing another sealing arrangement;

FIG. 11 is a partial sectional elevation similar to the left hand portion of FIG. 1 and showing a further embodiment of a dispensing device according to the invention;

FIG. 12 is a view similar to FIG. 11 showing another embodiment of dispensing device, and FIG. 13 is another view similar to FIG. 11 showing a further embodiment similar to that of FIG. 12.

DETAILED DESCRIPTION

Figure 1:
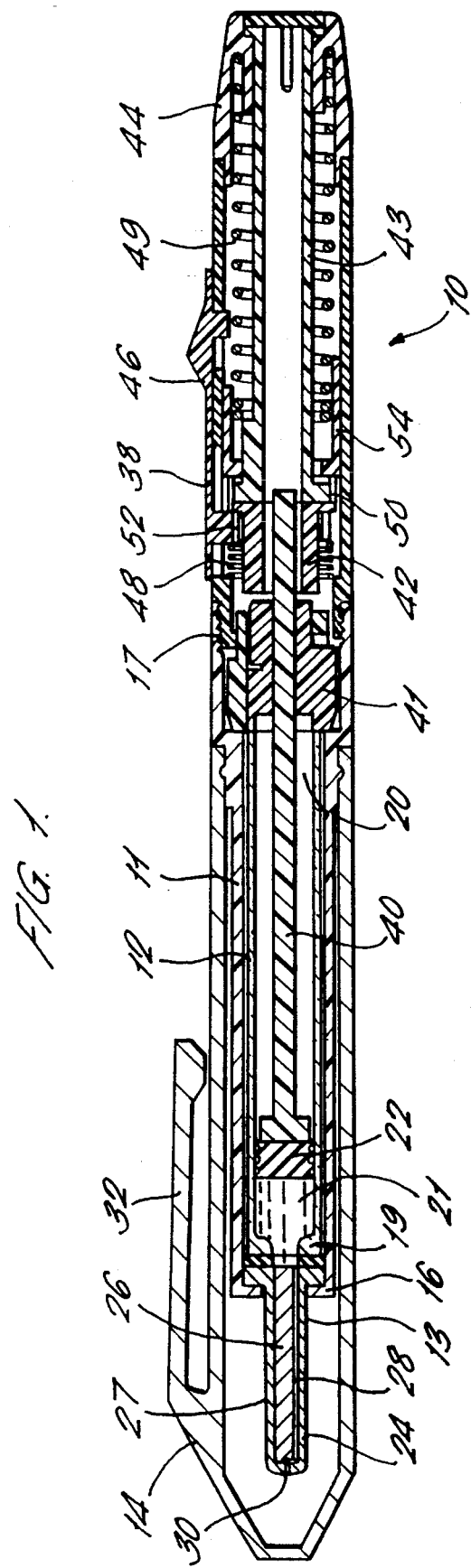
FIG. 1 is a sectional elevation through a dispensing device according to the invention.

Referring first to FIG. 1, there is illustrated a dispensing device intended for dispensing a liquid medicament in the form of a spray. The device is particularly suitable for dispensing liquid medicaments such as insulin and provides the medicament in the form of a spray which is particularly suitable for nasal administration of the medicament.

The dispensing device comprises a drive unit 10, the cartridge housing 11, a cartridge 12, a nozzle 13 and a protective cap 14.

The housing 11 is a cylindrical tube mainly closed off at one end 16 and internally threaded at its other end 17 for screw threaded connection to the drive unit 10. The housing is preferably of a transparent material.

Located within the housing is the cartridge 12 which is also cylindrical and tubular, closed off at one end 19 and open at its other end 20. The cartridge is initially substantially filled with liquid medicament 21, the liquid being retained in the cartridge by a sliding piston member 22 which is a sealing fit within the bore of the cartridge. Prior to insertion into the housing 11, the cartridge includes a seal (not shown in FIG. 1) over its end 19, the seal being removed or perforated when the cartridge is inserted into the housing. In use, the end 19 of cartridge 12 is in sealing contact with one end of the nozzle 13. In FIG. 1, the nozzle is located within end 16 of housing 11, a generally cylindrical part 24 of the nozzle projecting through the end 16 of housing 11.

The nozzle 13 is of the type designed to dispense a pressurised liquid passing through the nozzle in the form of a spray. The construction of the nozzle 13 may be for example, as described in published European Patent Application 0308100. The nozzle 13 comprises an inner component 26 and an outer component 27 nested together. The inner nested component is cylindrical and extends co-axially with the housing and includes an axially extending groove 28 which is overlayed by the other nested component 27 to define a flow path for dispensed liquid, the flow path communicating between an outlet orifice 30 formed in the other nested component and the interior of cartridge 12. Swirl inducing ducts (not shown in FIG. 1, but see 136 in FIG. 10) are provided either in the outer or inner nested component at the nesting ends of those components and extending generally transversely to the axis. When liquid is forced under pressure through the duct 28, the swirl inducing ducts cause the liquid to break up and be dispensed through the orifice 30 as a spray.

In use of the dispensing device, liquid is forced through nozzle 13 under pressure by the drive unit 10 which will be described in detail below. When the dispensing device is not in use, the protective cap 14 is placed in position as illustrated in FIG. 1, fitting over the nozzle 13 and housing 11, interengaging means being provided between the cap 14 and outer surfaces of housing 11 to retain the cap in position. The cap may include a spring clip 32 similar to a pen so that the dispensing device may be carried in the pocket in a similar manner to a pen. The dispensing device is of the pen type and has overall dimensions and shape similar to that of a reasonably large pen.

The drive unit 10 of the dispensing device has a housing 38 which, as described above, is screw threadedly connected to the cartridge housing 11. A plunger 40 extends from one end of drive unit housing 38 and the drive unit is operable to cause the plunger to move axially out of the housing 38 by a fixed distance determined by a dose selector 44 which is rotatably mounted at the end of housing 38 remote from plunger 40. Axial movement of the plunger 40 by said fixed distance causes the piston 22 to move by the same distance and expel a selected dose of the liquid medicament within cartridge 12 as described above.

The drive unit 10, as illustrated in FIG. 1, is of the kind described in published European Patent Application 0338806. The drive unit 10 is particularly described with reference to FIG. 3 of European Patent Application 0338806 and reference is hereby made to FIG. 3 of that publication and the accompanying description for a detailed description of the components of drive unit 10. The main components are the housing 38, the plunger 40 which slides in a plunger guide 41 and extends through a drive gear 42. The plunger has an integrally formed thread of large lead angle which cooperates with a corresponding internal thread in the bore of drive gear 42 so that rotation of the drive gear 42 causes axial movement of the plunger 40. The dose selector 44 is fixed to a drive sleeve 43, the drive sleeve 43 including a ratchet tooth or teeth which engage internal gear teeth 50 formed within an end of drive gear 42. A sliding trigger 46 is provided for actuating the drive unit 10. The trigger 46 is mounted for sliding movement axially relative to housing 38 and has an internally projecting spline or tooth 52 which engages, in a rest position of the trigger, gear teeth formed externally on the drive gear 42. A compression spring 48 urges the trigger towards its rest position. A helical spring 49 is located between the dose slector 44 and a spring retaining cap 54.

In use of the drive unit 10, the dose selector 44 is rotated relative to the housing 38 to select a desired dose of medicament to be dispensed. The dose selector 44 is calibrated for this purpose. Rotation of the dose selector rotates the drive sleeve 43 which turns within drive gear 42, the ratchet teeth engagement between drive sleeve 43 and drive gear 42 permitting this. During this pre-setting of the dose, the drive gear 42 is prevented from rotation in the housing 38 by its engagement with the trigger 46. The ratchet teeth engagement between drive sleeve 43 and drive gear 42 provides an audible clicking which also serves to indicate to a user of the device the level of dose which has been selected by the dose selector 44. When the trigger is released by sliding movement to the left as viewed in FIG. 1, it moves out of engagement with the drive gear 42 against the action of spring 48 thereby realeasing the drive gear 42. Spring 49 then unwinds to rotate the drive gear 42 and drive the plunger 40 axially also to the left as viewed in FIG. 1. The spring retaining cap 54 includes an internal projection which cooperates with the drive sleeve 43 to limit the rotational movement of the drive gear 42, thereby controlling the axial movement of the plunger 40. As described above, the axial movement of the plunger causes a dose of medicament to be dispensed through the nozzle 13.

When another dose is to be dispensed, a user of the device again rotates dose selector 44 to operate the plunger as described above. It will be appreciated that the plunger moves incrementally to the left as viewed in FIG. 1 on each actuation of the device. Initially the plunger extends only a small distance into the end of cartridge 12 and as doses are dispensed, the plunger continues to move to the left until it reaches a position similar to that shown in FIG. 1 when most the medicament has been dispensed and the cartridge is nearly exhausted. Further uses of the device by rotating the dose selector 44 and following the trigger 46 will cause the remaining medicament to be dispensed until the cartridge 12 is empty.

The main components of the dispensing device may then be reused. When housing 11 is unscrewed from drive unit 10, the cartridge 12 may be extracted and replaced by a fresh cartridge. The nozzle 13 may also be replaced at the same time. The drive unit may be reset to its starting position by retracting the plunger into the drive unit as described in European application 0338806.

The dispensing device 10 shown in FIG. 1 and described above shows the present invention its simplest form with the nozzle 13 being in direct communication with the cartridge 12 once the components of the device have been assembled.

It will be appreciated that it may be desirable to provide some form of sealing arrangement so that the medicament within the cartridge 12 is not in communication with the atmosphere for prolonged periods. Such an arrangement will be necessary if the cartridge stores sufficient medicament for use over an extended period of time and if the medicament concerned is of a type which denatures if exposed to the atmosphere over a period of time as in the case of, for example, insulin. A number of sealing arrangements may be incorporated into the dispensing device and some of these are illustrated in FIG. 2 to 10 together with other modifications of the dispensing device.

Figure 2:
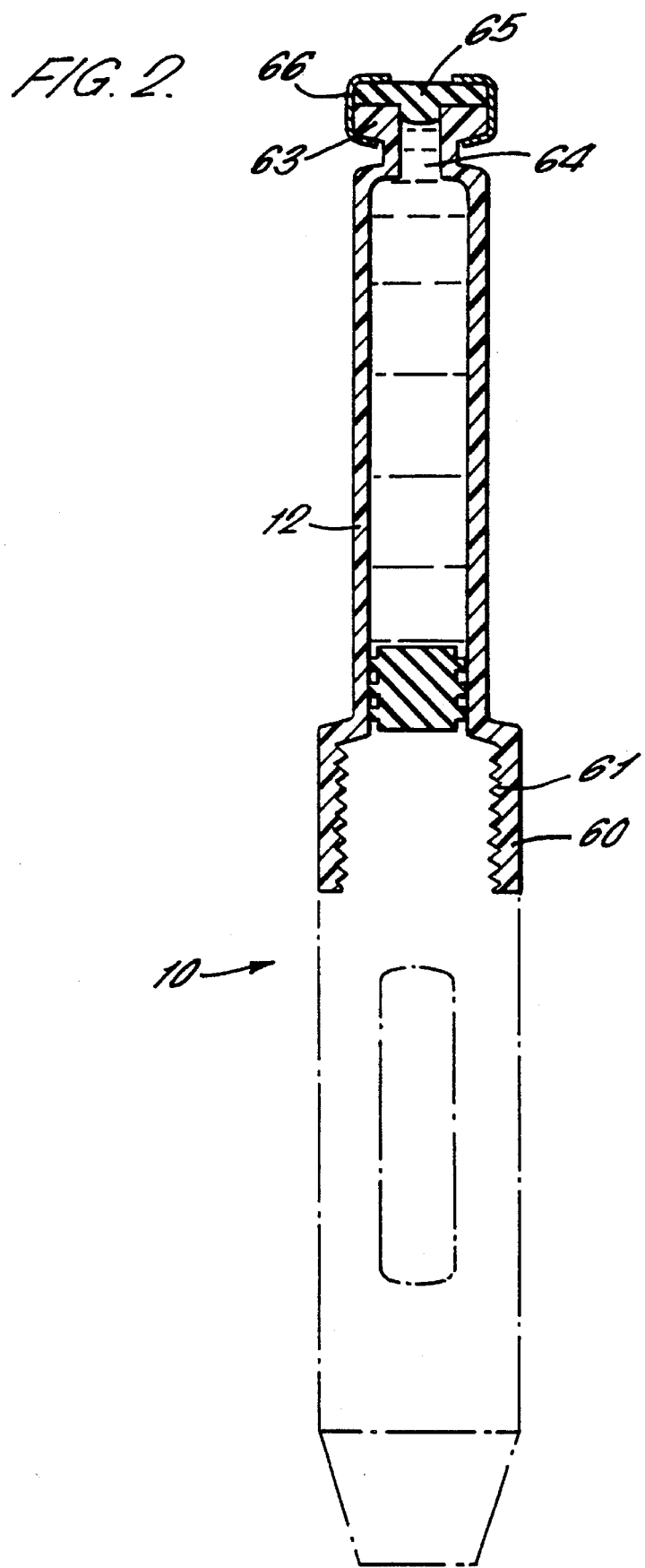
FIG. 2 is a diagramatic elevation of a second embodiment of a dispensing device according to the invention.

Referring first to FIG. 2, a modification of the dispensing device is illustrated in which the housing 11 is dispensed with. In FIG. 2, the cartridge 12 is formed from a plastics material and includes a flared end portion 60 having an internal screw thread 61 for cooperating engagement with the power unit 10. The arrangement shown in FIG. 2 is particularly suitable when the cartridge is made from a plastics material. Existing known cartridges 12 for medicaments such as insulin are usually formed from glass.

FIG. 2 also illustrates one possible sealing arrangement for the cartridge 12 prior to use. The cartridge 12 in FIG. 2 includes a neck 63 having a central aperture 64 which is closed off by a rubber seal 65 held in place by a ferrule 66. Such a sealing arrangement is of the type usually provided with a glass cartridge 12. If the cartridge 12 is made of a plastics material, a foil seal fixed to the plastic cartridge may be provided instead. Whatever form of initial seal is provided on the cartridge, it will be appreciated that it is necessary to remove or perforate that seal when the cartridge is to be used.

As mentioned above, initial removal or perforation of the seal from the cartridge 12 leaves the medicament open to the atmosphere and it is often desirable to provide an arrangement to reseal the cartridge beween uses of the device.

Figure 3:
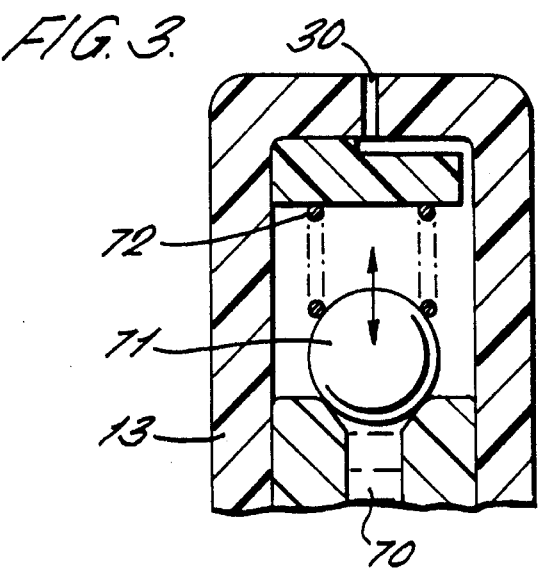
FIG. 3 is a diagramatic view of part of a nozzle of the dispensing device of FIG. 1 illustrating a first sealing arrangement for the nozzle.
Figure 4:
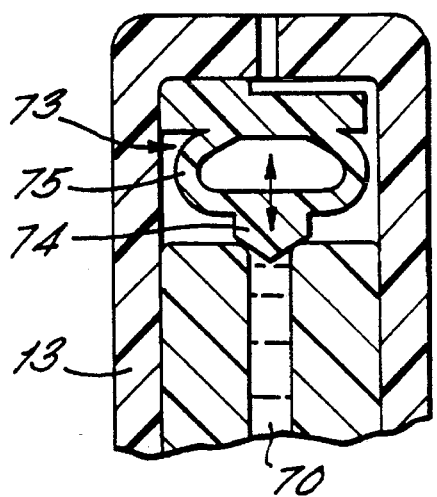
FIGS. 4 and 5 are views similar to FIG. 3 showing alternative sealing arrangements for the nozzle.
Figure 5:
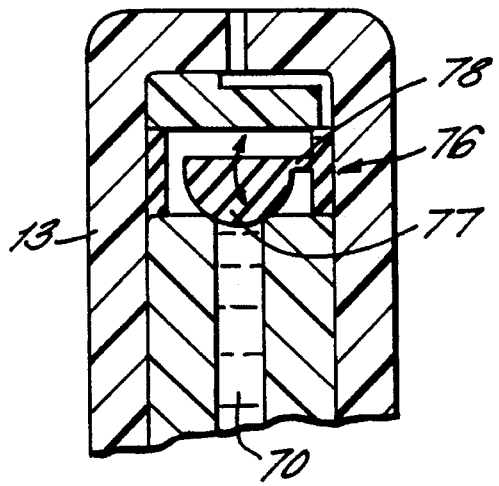

FIGS. 3, 4, and 5 illustrate sealing arrangements which may be incorporated into the nozzle 13. In each of FIGS. 3, 4 and 5 a simple one way valve mechanism is incorporated into the nozzle 13 adjacent the outlet orifice 30 and arranged to close off a flow path 70 through the nozzle.

In FIG. 3, the valve comprises a ball valve member 71 normally urged into its closed position by a spring 72. In FIG. 4, the valve comprises a plastics member 73 incorporating a valve portion 74 and a resilient portion 75. In FIG. 5 the valve 76 includes a valve member 77 connected by a resilient flap 78 to the body of the valve.

In each of FIGS. 3, 4 and 5, it will be seen that the valve is normally urged into a closed position and is opened by pressure of fluid being dispensed through the nozzle 13.

Figure 6:
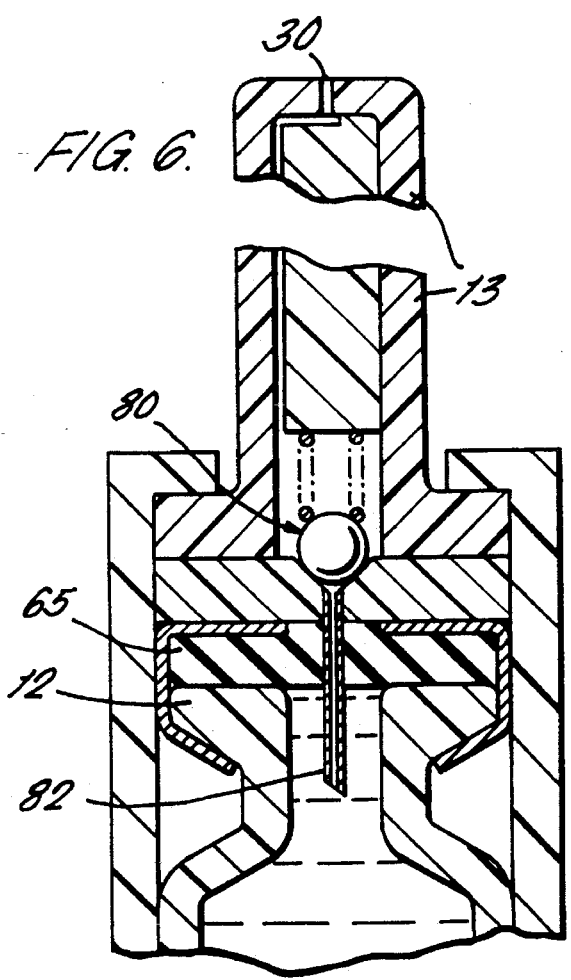
FIG. 6 is a further diagramatic view of the nozzle showing an alternative sealing arrangement.

FIG. 6 illustrates an alternative sealing arrangement in which a valve 80 is incorporated into the nozzle 13 at the end of the nozzle remote from outlet orifice 30 and adjacent to the cartridge 12. FIG. 6 illustrates a simple ball valve of the type shown in FIG. 3 but it will be appreciated that other one way valves of the types shown in FIGS. 4 and 5 may be incorporated into the same position as valve 80 in FIG. 6.

FIG. 6 also illustrates the provision on the nozzle 13 of a needle or spike 82 for perforating the seal 65 on the cartridge 12. In FIG. 6, the needle 82 is shown as of a relatively fine bore suitable for perforating a rubber seal 65 of the type shown in FIG. 2.

FIG. 7 illustrates a modified nozzle 83 which includes an axially inwardly projecting plastics spike 84 which is suitable for perforating a foil seal. FIG. 7 also illustrates an alternative sealing arrangement for the nozzle 83. In this arrangement an outer nested component 86 of the nozzle is rotatable relative to an inner nested component 87. A flow path 88 extending axially through the nozzle communicates with a transverse flow path 89 connecting to the outlet orifice 30 in one relative position of the nested components 86, 87 but is prevented from communication with flow path 89 when the nested components are rotated to a second relative rotational position. A key 91 may be provided on the outer nested component 86 as a visual indicator of the relative rotational positions of the nested components and for engagement by a cap of the device. The cap (not shown in FIG. 7) may engage the dispensing device by a twisting movement, the twisting movement also serving through the key 91 to rotate the nozzle 83 from open to shut positions and vice versa.

FIG. 8 illusrates a further embodiment of nozzle 100 in which relative rotational movement of two components of the nozzle serves to open and close a flow path through the nozzle. Nozzle 100 comprises a cylindrical outer component 101 including a spike 102 for penetrating a seal of the cartridge 12 and a cylindrical seat 103. An inner component 104 of the nozzle includes a flange 105 for sealing location in seat portion 103 and a cylindrical portion 106. Cooperating engagement means such as snap bands 107 are provided on the cylindrical portion 106 and within the seat 103 for retaining the inner and outer components of the nozzle assembled. A flow path 109 through the component 104 is arranged to align with an orifice 110 provided in the seat 103 offset from its axis. Rotation of component 104 relative to component 101 serves to open and close the flow path through the nozzle 100. A key 111 may be provided for indicating the position of the nozzle and also for engagement by a cap of the device as described above with reference to FIG. 7.

Figure 9:
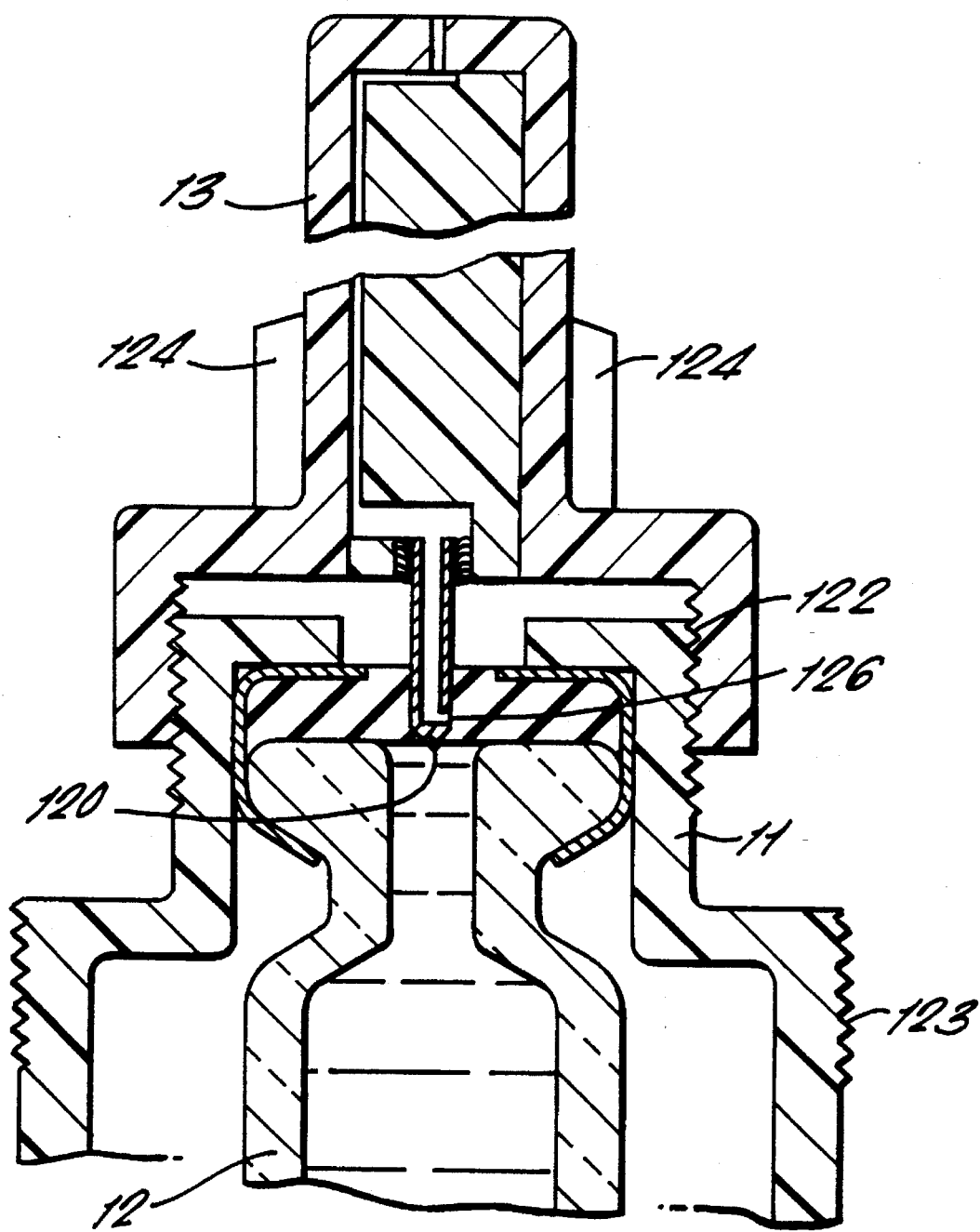
FIG. 9 is a diagramatic view similar to FIGS. 6 and 7 showing a further sealing arrangement.

FIG. 9 illustrates a further alternative sealing arrangement for the device in which sealing is effected by axial movement of a needle 120 which penetrates the initial seal of the cartridge 12. In FIG. 9, the nozzle 13 is connected to the housing 11 of the dispensing device by cooperating left hand threads 122 while a cap (not shown in FIG. 9) of the device is connected to the housing 11 by right hand threads 123. The cap is arranged to engage a key or keys 124 formed on the nozzle so that as the cap is screwed clockwise on to the threads 123, the nozzle 13 is caused to rotate anticlockwise by the threads 122 and thereby withdraw the needle 120 through the seal of the cartridge 12 to the position illustrated in FIG. 9 where a side hole 126 of the needle is sealed from the contents of the cartridge 12. Unscrewing the cap anticlockwise causes the nozzle to rotate clockwise and move the needle axially through the seal so that the side hole 126 is again in communication with the contents of cartridge 12.

Figure 10:
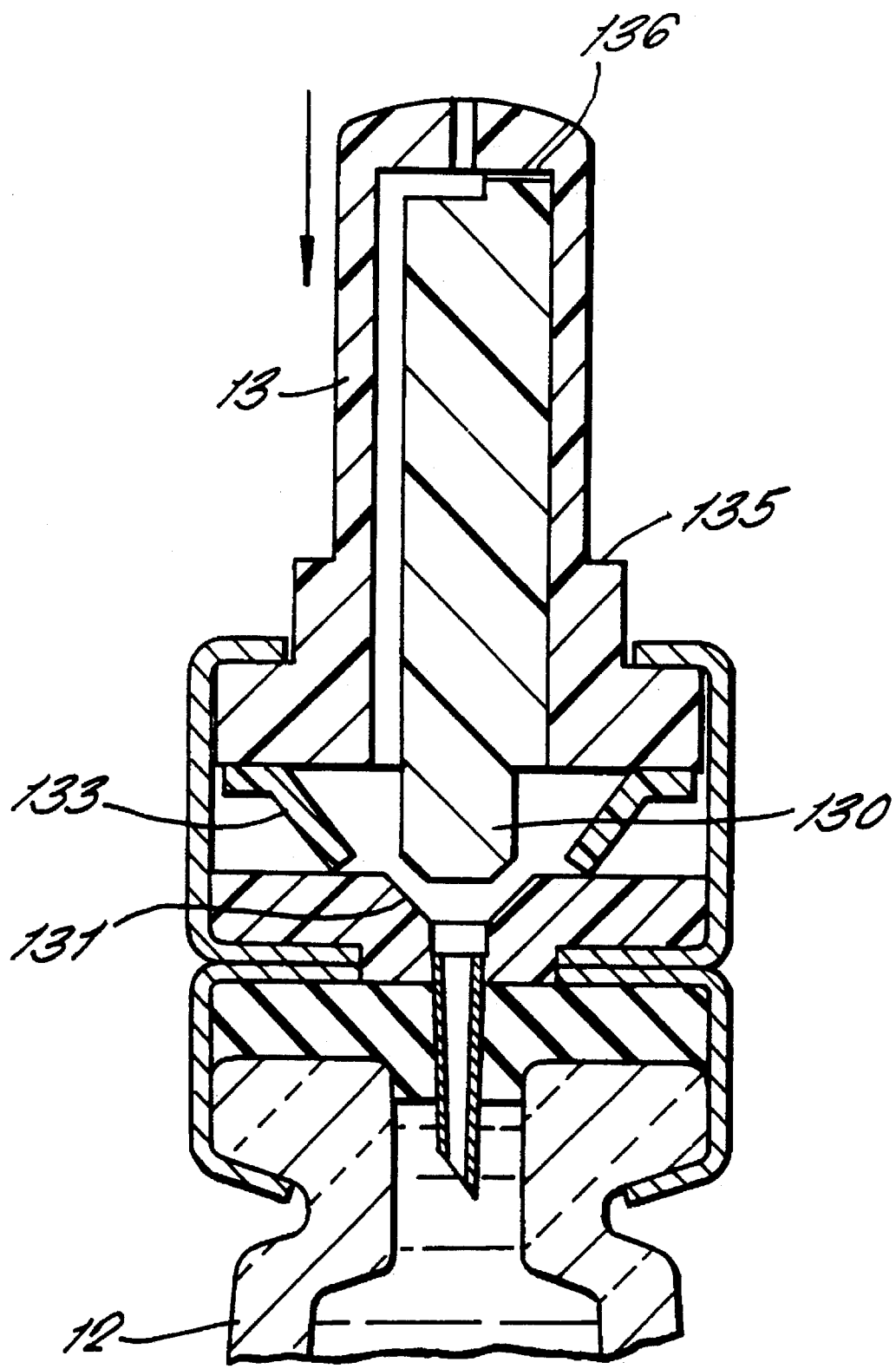
FIG. 10 is a further view similar to FIGS. 6 and 7 showing yet another sealing arrangement for the device.

FIG. 10 illustrates another sealing arrangement in which a sealing member 130 within the nozzle 13 is moved into and out of sealing engagement with a seat 131 by axial movement of the nozzle 13 relative to the cartridge 12. A spring member 133 is located within the nozzle 13 urging the sealing member 130 into the position shown in FIG. 10. The spring 133 may be a plastics disc spring, rubber bellows or other suitable spring device. The sealing member 130 is moved into its closed position by axially downward movement of the nozzle 13 (as viewed in FIG. 10). This axial movement is effected by engagement of a cap of the device (not shown in FIG. 10) with a shoulder 135 of the nozzle 13.

In all the embodiments of dispensing device described above, the medicament is dispensed by a trigger releasing energy stored in the drive unit which propels the piston 22 along the cartridge of medicament and thus forces medicament out through the nozzle of the device. In those embodiments described above in which a valve is provided to seal the medicament from the atmosphere between uses of the device, that valve is either opened by fluid pressure as the medicament is dispensed or the valve is opened mechanically prior to release of the energy in the drive unit, the drive unit again being triggered to release that energy.

FIGS. 11, 12 and 13 illustrate three further embodiments of dispensing device according to the invention in which a valve means is provided at the nozzle end of the device to seal the medicament from the atmosphere between uses of the device and in which that valve means is opened to allow the medicament to be released. In each of FIGS. 11, 12 and 13, the drive unit 10 for the device is not illustrated. In each case this drive unit 10 may be simplified from that described with reference to FIG. 1, in that no trigger device is required. Such drive units may be provided of known type in which movement of a plunger is controlled to advance the plunger by pre-selected distances in order to dispense pre-selected doses of medicament from a container of medicament.

Referring now to FIG. 11, a dispensing device 140 includes a generally cylindrical housing 141 having a stepped end 142 which is generally closed off and connects to a nozzle 143 of the device and includes at its other end a piston 22 which may be similar to the piston described in FIG. 1. A drive unit (not shown in FIG. 11) is arranged to move the piston 22 to the left as viewed in FIG. 11 by pre-selected distances corresponding to pre-selected doses of medicament stored in the device which are to be dispensed.

The stepped end 142 of the medicament cartridge 141 is closed off by a valve cap 145 having a central aperture 146 fixed to the end of cartridge 141 and trapping a valve seat 147 between the valve cap 145 and the open end of step portion 142 of cartridge 141.

The nozzle 143 of the device comprises outer and inner nested components 149 and 150 which define between them a flow path for medicament to be dispensed in similar manner to the nozzle 13 described with reference to FIG. 1, an axially extending channel 152 defined between the inner and outer components 149, 150 leading to a swirl chamber 153 and outlet orifice 154 of the device. The inner end of inner nested component 150 includes a tapered peg 156 which is fitted in a tapered bore of a valve core 158. The valve core 158 includes an enlarged portion 159, the shoulder of which engages the valve seat 147 to isolate the contents of cartridge 141 from the atmosphere when the device is not in use. When the portion 159 is unseated from valve seat 147, medicament may flow into the nozzle 143 through side holes 160 in the valve core 158 and thence through a flow path formed between tapered peg 156 and the bore in which it seats. This connects in turn with axial bore 152 in nozzle 143.

The inner and outer nested components 149, 150 of the nozzle 143 and the valve core 158 are fixed together to move as a single component. The assembly of nozzle and valve core is moved by a slider 162 including finger grips 163 which is fixed to a skirt portion 164 of the outer component 149 of the nozzle assembly. As shown in FIG. 11, the attachment of the slider 162 to the skirt portion 164 is by means of an inter-engaging annular bead and groove 166, 167 which snap fit together. The assembly of nozzle 143 and valve stem 158 is urged into its normally closed position by spring 169 located between an inner surface of outer nozzle component 149 and valve cap 145.

The dispensing device 140 also includes a cap 170 which fits over the cartridge 141 enclosing the nozzle assembly 143 and includes a clip 171 similar to a pen cap.

In use of the device 140, the cap 170 is first removed. The device is then pre-loaded to dispense a pre-selected quantity of medicament by selecting the required dose on a drive unit. The user then applies the nozzle 143 to the point at which the medicament is to be introduced (for example a nostril) and slides the slider 162 relative to the cartridge 141 thereby unseating the valve stem 158 from the valve seat 147 and allowing the medicament to be dispensed.

FIGS. 12 and 13 illustrate embodiments of dispensing device in which the medicament is again released by opening a valve at the nozzle end of the device but in FIGS. 12 and 13 the movement required to open the valve is axially to the left as illustrated in the figures rather than axially to the right as is the case with the embodiment of FIG. 11.

Referring now to FIG. 12, a dispensing device 180 again includes a cartridge 181 containing medicament to be dispensed and having a piston 22 in sliding sealing engagement with the inner surface of the cartridge. Movement of the piston is controlled by a drive unit (not shown in FIG. 12) but of a similar type to that described above. The other end of cartridge 181 includes a reduced diameter cylindrical portion 182 which is substantially closed off by a valve seat 183 which fits over the open end of reduced diameter portion 182 and is fixed thereto.

The dispensing device 180 has a nozzle 185 comprising inner and outer nested components 186, 187 which define between them a flow path leading to an outlet orifice 194 in similar manner to that described above. The inner end of inner component 186 is formed as a valve member 188 which forms a sealing engagement with valve seat 183 and is normally urged into its closed position by a spring 189.

The outer component 187 of nozzle assembly 185 includes a skirt portion 190 to which is fixed a slider 191, the slider being fixed to the skirt portion by the interengagement of an annular bead and groove in similar manner to the arrangement in FIG. 11. The spring 189 acts between the inner end of valve seat 183 and an inwardly directed annular flange on slider 191. A cap (not shown in FIG. 12) may be provided to contain the nozzle end of the dispensing device 180 when it is not in use and serves to prevent the ingress of dust and other like material.

In use of the dispensing device 180, the cap, if provided, is first removed and the device is then primed by pre-loading of the drive unit as described above with reference to FIG. 11. The valve formed by member 188 and seat 183 is then opened by an axial movement of the slider 191 relative to the cartridge 181 but, as discussed above, in a direction away from the main body of the cartridge rather than towards it. As the valve member 188 is unseated from seat 183, the medicament flows through a central aperture 193 in valve seat 183 and thence through the flow path defined between the inner and outer nested components of nozzle assembly 185 and through the outlet orifice 194.

FIG. 13 shows a further embodiment of dispensing device 200. The dispensing device 200 is similar to dispensing device 180 and like parts have been given the same reference numerals. However, in dispensing device 200, the component 201 providing the valve seat and the inner end of nozzle assembly 185 are designed to minimise the dead space in the device, that is the space in which medicament may reside after use of the device. In dispensing device 200 the valve seat component 201 is a tubular component having an annular flange 202. The inner part of tubular component 191 is fixed in the reduced diameter portion 182 of cartridge 181 and the flange 202 retains the spring 189 which is located between that flange and the inwardly directed annular flange of slider 191.

The other end of valve seat component 201 extends through a washer 205 and retaining cap 206 which fit within the outer component 187 of the nozzle assembly 185 and abut the inner nozzle component 186. The inner nozzle component 186 includes a valve member 208 which co-operates with a valve seat formed by the end of component 201. When the valve is opened, communication between the interior of cartridge 181 and the outlet orifice 194 is through a radial channel 209 formed between the inner nozzle component 186 and the washer 205 and thence through the flow path defined between the inner and outer nested components 186, 187 and to the outlet orifice 194.

The use of the dispensing device 200 shown in FIG. 13 is the same as dispensing device 180 described with reference to FIG. 12. The device is again primed and the medicament is then released by axial movement of slider 191 to the left relative to cartridge 181 as viewed in FIG. 13. This sliding movement unseats valve member 208 from the valve seat and allows medicament to flow through the flow path described above and out of the outlet orifice.

The invention is not limited to the embodiments described above and it will be appreciated that various modifications may be made. For example, a number of sealing arrangements for the device have been described with reference to FIGS. 3 to 10 and FIGS. 11 to 13. These sealing arrangements may be replaced by other variants.

Further, as has been discussed above, other drive units may replace the drive unit 10 described with reference to FIG. 1.

I claim:

1. A dispensing device comprising a multi-dose liquid container holding a plurality of doses of liquid to be dispensed, the plurality of doses of liquid being in direct contact with an interior surface of said multi-dose liquid container, an outlet nozzle positioned at an outlet end of said dispensing device, and said outlet nozzle including means to break-up a flow of liquid under pressure into a spray, a piston slidable in the multi-dose liquid container, said piston being in direct contact with the interior surface of the multi-dose container and with the liquid which is also in direct contact with the interior surface of the multi-dose liquid container, such that said piston, upon sliding, forces liquid out of the multi-dose liquid container under pressure, through the nozzle and out away from said dispensing device in a spray, mechanical drive means for moving the piston a predetermined distance to dispense a predetermined dose of liquid from the multi-dose liquid container, through said nozzle and out away from said dispensing device in a spray, the drive means including a dose selector for selecting the predetermined dose of liquid.

2. A device as claimed in claim 1 characterised in that the drive means includes a plunger (40) for moving the piston, movement of the dose selector determining subsequent movement of the plunger.

3. A device as claimed in claim 2 characterised in that movement of the dose selector stores energy in a spring (49), a trigger (46) being provided for releasing the spring and thereby moving the plunger.

4. A device as claimed in claim 1 characterised in that sealing means (65) is provided for selectively closing a flow path from the container through the nozzle.

5. A device as claimed in claim 4 characterised in that said sealing means comprise valve means (71) in the nozzle, the valve means being resiliently urged into a closed position and opened by flow of liquid under pressure from the container.

6. A device as claimed in claim 4 characterised in that said sealing means comprise means for moving one component of the nozzle relative to another component of the nozzle to open and close the flow path 7. A device as claimed in claim 4 characterised in that said sealing means comprises a spike (82) of the nozzle extending into the container through a seal (65) of the container and means for moving a part of the nozzle and the spike axially relative to the container.

8. A device as claimed in claim 3 further comprising sealing means for selectively closing a flow path from the container through the nozzle, and said sealing means comprises valve means normally urged into a closed position, and said valve means being urged into an open position by a flow of liquid under pressure produced by movement of said plunger following activation of said trigger.

9. A device as claimed in claim 4 characterised in that the sealing means comprise valve means normally urged into a closed position, the valve means being opened by relative movement between the container and the nozzle.

10. A device as claimed in claim 9 further comprising a manually operable sliding member fixed to the nozzle for moving the nozzle relative to the container.

11. A device as claimed in claim 9 characterised in that the valve means is located between the container and the nozzle.

12. A device as claimed in claim 11 characterised in that the valve means comprises a valve seat formed in a component fixed to the container and a valve member fixed to or integral with the nozzle and co-operable with the valve seat to close off the flow path from the container through the nozzle.

13. A device as claimed in claim 9 characterised in that the valve means is opened by relative axial movement of the nozzle towards the container.

14. A device as claimed in claim 9 characterised in that the valve means is opened by relative axial movement of the nozzle away from the container.

15. A device as claimed in claim 1 characterised in that the container, piston and nozzle form a disposable unit, said unit including means at an end remote from the nozzle for connecting said unit to the drive means.

16. A device as claimed in claim 10 in which the valve means is located between the container and the nozzle.

17. A dispensing device, comprising:

a multi-dose liquid container holding a plurality of doses of liquid medicament to be dispensed, the plurality of doses of liquid being in direct contact with an interior surface of said multi-dose liquid container;

an outlet nozzle positioned at an outlet end of said dispensing device, and said outlet nozzle including means to break-up a flow of liquid under pressure into a spray suitable for nasal administration of the liquid medicament;

a piston slidable in the multi-dose liquid container, said piston being in direct contact with the interior surface of the multi-dose container and with the liquid which is also in direct contact with the interior surface of the multi-dose liquid container, such that said piston, upon sliding, forces liquid in a continuous, uninterrupted flow first out of the multi-dose liquid container under pressure, then through the nozzle and then out away from said dispensing device in a spray; and mechanical drive means for moving the piston a predetermined distance to dispense a predetermined dose of liquid from the multi-dose liquid container, through said nozzle and out away from said dispensing device in a spray, the drive means including a dose selector for selecting the predetermined dose of liquid.

18. A dispensing device as recited in claim 17 wherein said liquid medicament in the liquid container is insulin.

* * * * *